United States Patent [19]

Monnier et al.

[11] Patent Number: 5,705,722
[45] Date of Patent: Jan. 6, 1998

[54] CONVERSION OF BIOMASS FEEDSTOCK TO DIESEL FUEL ADDITIVE

[75] Inventors: Jacques Monnier, Ottawa; Guy Tourigny, Nepean; Douglas W. Soveran, Regina; Alfred Wong, Vancouver; Edmund N. Hogan, Ottawa; Mark Stumborg, Swift Current, all of Canada

[73] Assignee: Natural Resources Canada, Ottawa, Canada

[21] Appl. No.: 517,421

[22] Filed: Aug. 21, 1995

Related U.S. Application Data

[63] Continuation-in-part of Ser. No. 269,090, Jun. 30, 1994, abandoned.

[51] Int. Cl.[6] ..................................................... C07C 1/00
[52] U.S. Cl. ............................ 585/240; 585/242; 585/733
[58] Field of Search .................................... 585/241, 240, 585/242, 733

[56] References Cited

U.S. PATENT DOCUMENTS

| | | | |
|---|---|---|---|
| 4,300,009 | 11/1981 | Haag et al. | 585/408 |
| 4,992,605 | 2/1991 | Craig et al. | 585/240 |
| 5,233,109 | 8/1993 | Chow | 585/241 |

Primary Examiner—Glenn A. Caldarola
Assistant Examiner—Bekir L. Yildirim

[57] ABSTRACT

A process is described for producing additives for diesel fuels having high cetane numbers and serving as fuel ignition improvers. In the process, biomass feedstock selected from (a) tall oil containing less than 0.5 wt % ash, less than 25 wt % unsaponifiables, up to 50 wt % diterpenic acids and 30 to 60 wt % unsaturated fatty acids, (b) wood oils from the pulping of hardwood species, (c) animal fats and (d) blends of said tall oil with plant or vegetable oil containing substantial amounts of unsaturated fatty acids or animal fats, is subjected to hydroprocessing by contacting the feedstock with gaseous hydrogen under hydroprocessing conditions in the presence of a hydroprocessing catalyst to obtain a product mixture. This product mixture is then separated and fractionated to obtain a hydrocarbon product boiling in the diesel fuel boiling range, this product being the high cetane number additive.

10 Claims, 1 Drawing Sheet

CONVERSION OF BIOMASS FEEDSTOCK TO DIESEL FUEL ADDITIVE

CROSS REFERENCE TO RELATED APPLICATION

This application is a continuation-in-part of U.S. patent application Ser. No. 08/269,090, filed Jun. 30, 1994, now abandoned.

FIELD OF THE INVENTION

This invention relates to a process for producing additives for diesel fuels having high cetane numbers and serving as fuel ignition improvers.

BACKGROUND OF THE INVENTION

The cetane number of diesel fuels is a measure of the ignition quality of the fuel. Fuels having a low cetane number frequently may be characterized by poor cold weather starting, long ignition delays, increased combustion noise and even misfiring.

Methods of improving the cetane number of fuels have taken on increasing importance as the refinery product slate has changed and as the quality of the crude feedstocks has declined. The heavier crudes currently being processed normally produce less virgin middle distillate, and the distillate which is produced tends to be of a lower quality.

Many different approaches are described in the literature for improving the cetane rating of diesel fuels. One recent solution is described in Craig and Soveran, U.S. Pat. No. 4,992,605 issued Feb. 12, 1991. That patent describes the production of high cetane number additives by the hydroprocessing of a feedstock selected from canola oil, sunflower oil, soybean oil, rapeseed oil, palm oil and fatty acid fractions of tall oil. The cetane enhancer is typically admixed with diesel fuel in the range of 5 to 30% by volume.

Tall oil is typically obtained as a by-product in the Kraft pulping of pine and spruce trees. Canadian tall oil has very little economic value for pulp mills due to its very small share of the North American markets for fatty acids (paints) and resin acids (paper sizing). Most Canadian pulp mills do not sell tall oil but dispose of it by burning in chemical recovery boilers, power boilers or lime kilns. However, because of the low cost of natural gas which is the alternative fuel for power boilers and lime kilns, and because of potential problems in burning tall oil soap in chemical recovery boilers, there is a need for new market outlets for tall oil.

In U.S. Pat. No. 4,992,605 it was found that a fatty acid fraction of tall oil could be used as feedstock in the production of high cetane number additives. However, crude tall oil itself has not been found to be a satisfactory feedstock for this purpose. Vataru et al U.S. Pat. No. 4,857,073, issued Aug. 15, 1989, describes the use of tall oil fatty imidazoline as a diesel fuel additive.

SUMMARY OF THE INVENTION

According to the present invention it has surprisingly been discovered that highly effective biomass feedstock for producing high cetane number additives for diesel fuels may be selected from (a) tall oil containing less than 0.5 wt % ash, less than 25% wt % unsaponifiables, up to 50 wt % diterpenic acids and 30 to 60 wt % unsaturated fatty acids, (b) wood oils from the pulping of hardwood species, (c) animal fats and (d) blends of the above tall oil with plant or vegetable oils containing substantial amounts of fatty acids or with animal fats.

The tall oil may be a high quality tall oil which already meets the above specifications or it may be a crude tall oil which has been processed to remove undesirable components, such as ash and unsaponifiables, e.g. a depitched tall oil. The depitching (thermal evaporation) reduces both unsaponifiables and ash in the tall oil. The unsaponifiables can also be removed by procedures such as solvent extraction, solid-phase adsorption or by liquid chromatography. Ash may also be removed by washing the tall oil with water. A typical crude oil may contain 30–60 wt % fatty acids, 20–50 wt % diterpenic acids (also known as rosin or resin acids) and 10–40 wt % unsaponifiables.

The hardwood oils are typically obtained from the pulping of hardwoods, such as aspen or birch. T typical hardwood oil may contain 30–70 wt % unsaturated fatty acids, 30–70 wt % unsaponifiables and substantially no diterpenic acids. When it is necessary to remove any unsaponifiables or ash from the hardwood oils, this can be done in the same manner as with tall oil.

The animal fats are typically yellow grease, animal tallow, etc. and may also include waste restaurant oils containing animal fats and vegetable oils.

It has surprisingly been found that it is not only the unsaturated fatty acids in tall oil that can be converted to cetane improvers, but the diterpenic acids and unsaponifiables can also be converted to cetane products, provided the tall oil compositions meet the requirements of the present invention as stated above. It has also surprisingly been discovered that especially good yields of cetane improvers can be obtained if a mixed feedstock is used comprising the tall oil feedstock of the present invention mixed either with plant or vegetable oil containing substantial amounts of fatty acids or with animal fats. The oils may include canola oil, sunflower oil, soybean oil, rapeseed oil, palm oil, etc. and the animal fats may include yellow grease, animal tallow, etc. Significantly better yields of cetane improvers are obtained when the mixed feedstocks are used than could be predicted by calculation from the yields obtained with single feedstocks.

The cetane enhancers according to the invention is preferably added to diesel fuel in amounts in the range of about 5 to 30% by volume.

In the process of the present invention, the biomass feedstock is subjected to hydroprocessing by contacting the feedstock with gaseous hydrogen under hydroprocessing conditions in the presence of a hydroprocessing catalyst to obtain a product mixture. This product mixture is separated and then fractionated to obtain a hydrocarbon product boiling in the diesel fuel boiling range.

The catalysts suitable for the process of this invention are commercial hydroprocessing catalysts, including cobalt-molybdenum (Co-Mo) catalysts, nickel-molybdenum (Ni-Mo) catalysts, or other transition metal based catalysts used for hydroprocessing.

The hydroprocessing temperature should be at least 350° C. and preferably at least 370° C. The normal optimum operating temperature is in the range of about 370°–450° C.

The hydrogen pressure can vary quite widely and is preferably in the range of about 4 MPa to about 15 MPa. The liquid hourly space velocity (LHSV) can also vary quite widely within the range of about 0.5–5.0 $hr^{-1}$.

DESCRIPTION OF THE PREFERRED EMBODIMENTS

Figure 1:
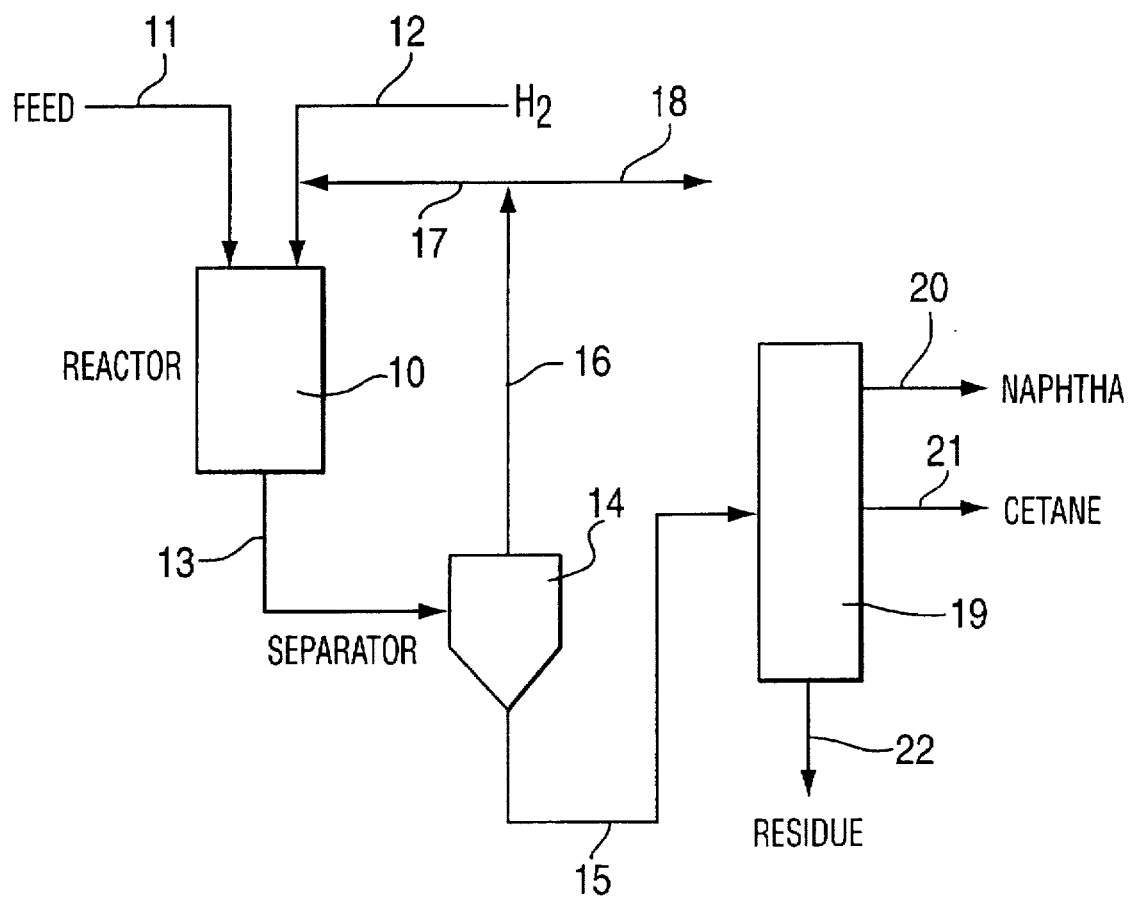
FIG. 1 is a flow sheet of a preferred process for carrying out the present invention.

FIG. 1 shows an automated semi-pilot hydrotreating reactor system used for testing the invention. This included a 700 ml stainless steel tubular reactor 10 having a length of 174 cm and an I.D. of 2.28 cm. A downflow configuration was used with biomass feedstock 11 and hydrogen 12 being fed from the top to simulate a trickle-bed reactor. A six point thermocouple (not shown) measured temperatures in the catalyst bed within reactor 10 at various locations along the reactor center approximately 12.7 cm apart. A five-zone furnace (not shown) was used to heat the reactor, with each power output being independent and controlled using the corresponding reactor wall temperature.

The hydrotreated product was withdrawn from the bottom of reactor 10 via line 13 and fed to a gas/liquid separator 14, where is was divided into a liquid stream 15 and a gaseous stream 16. The gaseous stream 16 was either recycled as part of the hydrogen input 12 or fed via line 18 as fuel gas for burners. The liquid stream 15 was fed to a distillation column 19 where it was fractionated into a naphtha stream 20, a middle distillate or cetane stream 21 which is the cetane improver of the invention and a residue stream 22 which can be used as fuel for boilers.

The depitched tall oil used in the process of this invention is obtained by treating a crude tall oil. Unsaponifiables are normally removed by evaporation, e.g. by means of a thin-film evaporator (TFE). This system operates with a short contact time (5 to 10 seconds), low pressure (5 to 10 mmHg vacuum) and moderate temperature (300° to 320° C.), which minimizes damage to thermally sensitive tall oil components. After removing unsaponifiables, the depitched tall oil may be processed through several further distillation stages for the fractionation of fatty acids, diterpenic acids, etc. The desired properties of the finished depitched tall oil include light colour, low ash content and high acid number. A preferred depitched tall oil for use in this invention is one containing about 5-20 wt %, more preferably about 5-15 wt %, of unsaponifiables and less than 0.5 wt % ash.

A crude tall oil from a Western Canadian source was depitched using a thin-film evaporator and the results are shown in Table A below:

TABLE A

|  | Crude Tall Oil | Depitched Tall Oil |
|---|---|---|
| Wet Method |  |  |
| Unsaponifiables, % | 20–30 | 12–16 |
| Acid number | 115–145 | 140–160 |
| Colour | dark brown | brown |
| Ash, % | 0.02–0.1 | trace |
| Acidity, pH units | 4.2–4.4 | 6–7 |
| GC Analysis |  |  |
| Beta-sitosterols, % | 2.5–4.0 | trace |
| Diterpene alcohols/ aldehydes, % | 1.0–4.0 | 1.5–5.0 |

EXAMPLE 1

A test was carried out using the above reactor. A commercial nickel-molybdenum or alumina catalyst, available under the trade mark CRITERION 424, was supplied in the form of extrudates. The catalyst bed contained about 270 g of extrudates and 163 g of silicon carbide diluent (20–48 mesh) corresponding to a catalyst to diluent ratio of 2:1 in volume.

The catalyst was activated by presulfiding the nickel and molybdenum oxides active sites supported on alumina. The catalyst was dried and then sulfided using a mixture of 2.5 wt % $CS_2$ in a highly stable diesel fuel.

The feedstock used was a commercial depitched tall oil containing 52 wt % fatty acids, 30 wt % resin acids and 15 wt % unsaponifiable components. It had an ASTM acid number of 158. The tall oil was filtered to remove all solids that precipitated during storage.

With the reactor at a temperature of 375° C. the depitched tall oil was fed in as feedstock. The actual test was performed at a reactor temperature of 410° C., hydrogen pressure of 8.3 MPa, and 280 mL/h depitched tall oil (0.8 $h^{-1}$ liquid space velocity). The depitched tall oil was spiked with 1000 ppm sulphur using $CS_2$ to avoid loss of sulphided active sites on the catalyst surface and maintain catalyst activity.

Product characteristics were monitored to assess catalyst performance and stability. Samples of liquid and gaseous products were collected and product yields were calculated for each sample. These results are shown in Table 1 below. On average, 80 g of hydrocarbon liquids (organic phase) was produced per 100 g of depitched tall oil (DPTO) and 8 g of water and water-soluble products (aqueous phase).

TABLE 1

Yields of products from catalytic hydroprocessing of DPTO at 410° C. and 8.3 MPa

| Sample # | 1 | 2 | 3 | 4 |
|---|---|---|---|---|
| Cumulative Operating Hours | 55.75 | 352.92 | 399.75 | 496.65 |
| Sampling period (h) | 21.25 | 21.00 | 19.00 | 43.66 |
| Production (g/100 g DPTO) |  |  |  |  |
| Liquid | — | 84.1 | 87.3 | 82.5 |
| Hydrocarbons | — | 77.3 | 80.8 | 76.3 |
| Aqueous phase | — | 6.8 | 6.5 | 6.2 |
| All gases except $H_2$ | — | 14.3 | 12.6 | 20.6 |

All products were characterized for density and boiling distribution obtained by simulated distillation (ASTM D-2887). The data are reported in Table 2, with the product density varying between 0.8379 g/ml and 0.8537 g/ml, increasing slightly with time on stream. On average, the 10% cut point was less than 90° C., the 50% cut point was about 312° C. and the 90% cut point between 360° C. and 410° C.

| Sample # | 1 | 2 | 3 | 4 |
|---|---|---|---|---|
| Density (g/mL) | 0.8392 | 0.8491 | 0.8485 | 0.8537 |
| Boiling point distribution (ASTM D-2887) |  |  |  |  |
| IBP (°C.) | 61 | 68 | 38 | 69 |
| 10% (°C.) | 176 | 174 | 165 | 171 |
| 50% (°C.) | 307 | 310 | 309 | 310 |
| 90% (°C.) | 361 | 398 | 400 | 409 |
| FBP (°C.) | 471 | 516 | 521 | 534 |
| Product Distribution (vol %) |  |  |  |  |
| Naphtha (IBP-190° C.) | 11.7 | 11.8 | 13.6 | 12.9 |
| Middle dist. (190–343°) | 73.3 | 65.7 | 63.6 | 62.1 |
| Residue (+343° C.) | 15.0 | 22.5 | 22.8 | 25.0 |

The following Table 3 represents a typical boiling point distribution obtained by ASTM D-86 distillation.

TABLE 3

| Fraction of products distilled off (vol %) | Boiling point (°C.) Sample #3 | Boiling point (°C.) Sample #20 |
|---|---|---|
| Initial Boiling Point - IBP | 100 | 116 |
| 10 | 197 | 189 |
| 20 | 254 | 251 |
| 30 | 273 | 277 |
| 40 | 292 | 295 |
| 50 | 297 | 303 |
| 60 | 304 | 308 |
| 70 | 309 | 325 |
| 80 | 317 | 348 |
| 90 | 337 | 396 |
| End Point (EP) | 382 | 404 |
| Recovery | 98.0 vol % | 97.0 vol % |
| Residue | 1.5 vol % | 2.0 vol % |
| Loss | 0.5 vol % | 1.0 vol % |

Product samples were blended to form a composite product which was then fractionated using an ASTM D-2892 distillation unit. The oil contained 80 wt % middle distillates (190°–343° C), 11 wt % naphtha (<190° C.) and 9 wt % residue (+343° C.).

Engine tests (ASTM D 613) indicated that the composite sample of hydrotreated depitched tall oil products had a cetane number of 52 and the diesel fuel additive, a cetane number of 56. This means that blending 25 wt % of the above additive in a poor diesel fuel basestock will raise the cetane number of the blended product above the required minimum of 40.

EXAMPLE 2

Using a small bench scale reactor of similar design to that described in Example 1 and the process as described in Example 1, a hydrotreating process was carried out using as feedstock a wood oil obtained from the pulping of aspen. The oil sample Aspen A contained 60 wt % unsaturated fatty acids and 40 wt % unsaponifiables, while sample Aspen B contained 58 wt % unsaturated fatty acids and 42 wt % unsaponifiables. The reaction was carried out at an average reactor temperature of 380° C., hydrogen pressure of 4 MPa and 1.0 h$^{-1}$ liquid space velocity.

Samples of liquid and gaseous products were collected and product yields were calculated. The results are shown in Table 4 below.

TABLE 4

Aspen Tall Oil Experiments Yield Summary

|  | Aspen A | Aspen B |
|---|---|---|
| Reactor Temp. (°C.) | 390 | 370 |
| Product Yields (wt % feed) | | |
| Hydrocarbon | 86.9 | 92.3 |
| Supercetane | 49.0 | 48.1 |
| Gas | 4.6 | 4.0 |
| Water | 11.6 | 1.8 |
| Simulated Distillation (wt % of the hydrocarbon product) | | |
| IBP-204° C. | 6.5 | 3.9 |
| 204–343° C. (diesel fraction) | 56.4 | 52.1 |
| 343° C.+ | 37.1 | 44.0 |
| Approximate Cetane No. | 70 | 65 |

EXAMPLE 3

Using the apparatus and process as described in Example 2, a hydrotreating process was carried out using as feedstock Finnish tall oil. This tall oil contained 45 wt % unsaturated fatty acids, 15 wt % unsaponifiables and 0.5 wt % ash. The reaction was carried out at a temperature of 400° C. and a hydrogen pressure of 8.3 MPa, using a commercial nickel-molybdenum catalyst on an alumina support.

The yield results and product analysis are summarized in Table 5 below:

TABLE 5

| Products | Experiment No. | | | | |
|---|---|---|---|---|---|
| Yields (wt % feed) | 94-01A | 94-01B | 93-01C | 94-01D | 94-01E |
| Hydrocarbon | 84.6 | 85.7 | 81.0 | 84.7 | 80.7 |
| Water | 7.5 | 7.4 | 6.8 | 6.9 | 6.8 |
| Gas | 5.2 | 7.4 | 9.6 | 9.4 | 8.4 |
| Distillate (204–343° C.) | 63.0 | 62.3 | 58.9 | 60.3 | 56.8 |
| Hydrocarbon Analysis | | | | | |
| Density (kg/m$^3$ @ 25° C.) | 821.0 | 822.3 | 822.8 | 825.4 | 826.0 |
| Simulated Distillation (wt % of hydrocarbon product) | | | | | |
| IBP-204° C. | 8.6 | 8.2 | 8.3 | 7.6 | 8.1 |
| 204–343° C. | 74.5 | 72.7 | 72.7 | 71.2 | 70.4 |
| 343° C.+ | 16.9 | 19.1 | 19.0 | 21.2 | 21.5 |

The 204°–232° C. fraction (cetane) had a cetane number of approximately 80.

EXAMPLE 4

Using the apparatus and process as described in Example 2, a hydrotreating process was carried out using as feedstock restaurant yellow grease obtained from Rothsay Ltd. of Toronto. It had the following fatty acid composition:

| Fatty Acid | Wt. % |
|---|---|
| C12:0 | 0.2 |
| C14:0 | 0.9 |
| C14:1 | ND |
| C15:0 | ND |
| C16:0 | 14.1 |
| C16:1 | 1.9 |
| C17:0 | 0.4 |
| C18:0 | 10.6 |
| C18:1 | 57.8 |
| C18:2 | 12.2 |
| C18:3 | 0.4 |
| C20:0 | 0.5 |
| C20:1 | 0.7 |
| C22:0 | 0.3 |
| Other | ND |
| Total | 100.00 |

The reaction was carried out at a temperature of 370° C. and a hydrogen pressure of 8.3 MPa, using a commercial nickel-molybdenum catalyst on an alumina support. The yield results and product analysis are summarized in Table 6 below:

TABLE 6

| Products | Experiment No. | | | | |
|---|---|---|---|---|---|
| Yields (wt % feed) | 94-05A | 94-05B | 93-05C | 94-05D | 94-05E |
| Hydrocarbon | 84.4 | 84.1 | 83.2 | 85.3 | 84.2 |
| Water | 8.6 | 9.0 | 8.1 | 8.8 | 7.8 |
| Gas | 3.2 | 3.4 | 6.7 | 6.4 | 6.8 |
| Distillate (204–343° C.) | 80.7 | 79.8 | 79.1 | 81.0 | 79.8 |

TABLE 6-continued

| Products | Experiment No. | | | | |
|---|---|---|---|---|---|
| Yields (wt % feed) | 94-05A | 94-05B | 93-05C | 94-05D | 94-05E |
| Hydrocarbon Analysis | | | | | |
| Density (kg/m³ @ 25° C.) | 773.3 | 774.4 | 773.5 | 773.7 | 774.0 |
| Simulated Distillation (wt % of hydrocarbon product) | | | | | |
| IBP-204° C. | 1.3 | 1.2 | 1.2 | 1.2 | 1.2 |
| 204-343° C. | 95.5 | 94.8 | 95.1 | 95.0 | 94.8 |
| 343° C.+ | 3.1 | 4.0 | 3.7 | 3.8 | 4.0 |

The 204°–343° C. fraction (cetane) had an approximate cetane number of greater than 90.

EXAMPLE 5

Using the apparatus and process as described in Example 2, a hydrotreating process was carried out using as feedstock animal tallow obtained from West Coast Reduction Ltd. of Vancouver. It had the following fatty acid composition:

| Fatty Acid | Wt. % |
|---|---|
| C12:0 | ND |
| C14:0 | 3.4 |
| C14:1 | 0.6 |
| C15:0 | 0.6 |
| C16:0 | 25.4 |
| C16:1 | 3.1 |
| C17:0 | 1.7 |
| C18:0 | 17.4 |
| C18:1 | 41.2 |
| C18:2 | 3.3 |
| C18:3 | ND |
| C20:0 | 0.5 |
| C20:1 | 0.5 |
| C22:0 | 0.3 |
| Other | 1.9 |
| Total | 100.00 |

The reaction was carried out at a temperature of 370° C. and a hydrogen pressure of 8.3 MPa, using a commercial nickel-molybdenum catalyst on an alumina support. The yield results and product analysis are summarized in Table 7 below:

TABLE 7

| Products | Experiment No. | | | | |
|---|---|---|---|---|---|
| Yields (wt % feed) | 94-06A | 94-06B | 93-06C | 94-06D | 94-06E |
| Hydrocarbon | 82.4 | 81.8 | 81.6 | 83.3 | 82.6 |
| Water | 8.9 | 9.9 | 9.6 | 8.9 | 9.3 |
| Gas | 1.7 | 7.0 | 7.5 | 8.3 | 8.3 |
| Distillate (204-343° C.) | 81.8 | 80.8 | 80.8 | 82.2 | 81.3 |
| Hydrocarbon Analysis | | | | | |
| Density (kg/m³ @ 25° C.) | 773.0 | 773.0 | 771.9 | 771.6 | 771.7 |
| Simulated Distillation (wt % of hydrocarbon product) | | | | | |
| IBP-204° C. | 0.5 | 0.5 | 0.5 | 0.6 | 0.7 |
| 204-343° C. | 99.2 | 98.8 | 99.0 | 98.7 | 98.4 |
| 343° C.+ | 0.3 | 0.7 | 0.5 | 0.7 | 0.9 |

The 204°–343° C. fraction (cetane) had an approximate cetane number of greater than 90.

EXAMPLE 6

Using the apparatus and process as described in Example 2, a hydrotreating process was carried out using as feedstock waste restaurant oil obtained from a commercial source. This waste oil was a mixture of restaurant yellow grease and used vegetable or plant oil.

The reaction was carried out at a temperature of 370° C. and a hydrogen pressure of 8.3 MPa, using a commercial nickel-molybdenum catalyst on an alumina support. The yield results and product analysis are summarized in Table 8 below:

TABLE 8

| Products | Experiment No. | | | | |
|---|---|---|---|---|---|
| Yields (wt % feed) | 94-03A | 94-03B | 93-03C | 94-03D | 94-03E |
| Hydrocarbon | 84.0 | 85.4 | 86.8 | 85.7 | 86.2 |
| Water | 7.5 | 7.4 | 6.8 | 6.9 | 6.8 |
| Gas | 9.9 | 8.4 | 8.6 | 10.4 | 9.9 |
| Distillate (204-343° C.) | 77.6 | 70.6 | 64.0 | 77.0 | 71.8 |
| Hydrocarbon Analysis | | | | | |
| Density (kg/m³ @ 25° C.) | 779.5 | 793.5 | 808.4 | 870.4 | 792.0 |
| Simulated Distillation (wt % of hydrocarbon product) | | | | | |
| IBP-204° C. | 1.5 | 1.3 | 1.3 | 1.3 | 1.2 |
| 204-343° C. | 92.4 | 82.7 | 73.7 | 91.9 | 83.8 |
| 343° C.+ | 6.1 | 16.0 | 25.0 | 6.8 | 15.0 |

The 204°–343° C. fraction (cetane) had an approximate cetane number of over 90.

EXAMPLE 7

Using the apparatus and process as described in Example 2, a hydrotreating process was carried out using as feedstock a mixture of 75 vol. % depitched tall oil as described in Example 1 and 25 vol. % canola oil as described in U.S. Pat. No. 4,992,605.

The reaction was carried out at a temperature of 400° C. and a hydrogen pressure of 8.3 MPa, using a commercial nickel-molybdenum catalyst on an alumina support. The yield results and product analysis are summarized in Table 9 below:

TABLE 9

| Products | Experiment No. | | | | |
|---|---|---|---|---|---|
| Yields (wt % feed) | 94-04A | 94-04B | 93-04C | 94-04D | 94-04E |
| Hydrocarbon | 83.8 | 73.7 | 82.0 | 84.1 | 74.7 |
| Water | 7.0 | 7.1 | 7.3 | 7.4 | 7.5 |
| Gas | 4.8 | 4.2 | 6.8 | 6.7 | 6.4 |
| Distillate (204-343° C.) | 69.5 | 60.9 | 67.9 | 69.7 | 62.0 |
| Hydrocarbon Analysis | | | | | |
| Density (kg/m³ @ 25° C.) | 802.9 | 804.8 | 806.0 | 805.8 | 805.5 |
| Simulated Distillation (wt % of hydrocarbon product) | | | | | |
| IBP-204° C. | 6.7 | 5.9 | 5.5 | 5.4 | 5.7 |
| 204-343° C. | 83.0 | 82.6 | 82.8 | 82.9 | 83.8 |
| 343° C.+ | 10.3 | 11.5 | 11.7 | 11.7 | 11.3 |

The 204°–343° C. fraction (cetane) had an approximate cetane number of over 90.

EXAMPLE 8

A further comparative study was carried out to examine a synergistic result of mixing tall oil with either vegetable (plant) oil or an animal fat. The tests were conducted using the same apparatus and processing conditions as in Example 7 and using as feedstock:
(1) depitched tall oil alone
(2) canola oil alone
(3) tallow alone
(4) a blend of 7% depitched tall oil and 25% canola oil
(5) a blend of 70% depitched tall oil and 30% tallow.
The yields obtained are shown in Table 10 below:

TABLE 10

| Test Run | Feedstock | Yield of Normal Alkanes (C6–C24) |
|---|---|---|
| CDS 9203 | 100% depitched tall oil | 25.8 wt % |
| CDS 9403 | 100% canola oil | 72.5 wt % |
| CDS 9406 | 100% tallow | 91.6 wt % |
| CDS 9404 | 75% depitched tall oil + 25% canola oil | 56.5 wt % |
| Calculated | 75% depitched tall oil + 25% canola oil | 37.5 wt % |
| CDS 9503 | 70% depitched tall oil + 30% tallow | 52.2 wt % |
| Calculated | 70% depitched tall oil + 30% tallow | 45.5 wt % |

From the above table it can be seen that for both of the blended feedstocks the yields were significantly higher than could have been predicted by calculation from the yields obtained with the individual feedstocks.

We claim:

1. A process for producing a liquid hydrocarbon product effective as a diesel fuel cetane number improver, comprising:

(a) hydroprocessing a biomass feedstock comprising tall oil containing less than 0.5 wt % ash, 5–20 wt % unsaponifiables, 20–50 wt % diterpenic acids and 30 to 60 wt % unsaturated fatty acids, by contacting the tall oil feedstock with gaseous hydrogen under hydroprocessing conditions, including a temperature of at least 350° C., in the presence of a hydroprocessing catalyst to convert the feedstock into a mixture of compounds including liquid hydrocarbons in the diesel fuel boiling range, (b) separating the mixture of compounds; and (c) fractionating the mixture of compounds to obtain a high cetane number product boiling in the diesel fuel range.

2. A process according to claim 1 wherein the hydroprocessing conditions include a temperature in the range from about 370° C. to about 450° C., a hydrogen partial pressure in the range of about 4 MPa and about 15 MPa and a liquid hourly space velocity of about 0.5 to 5.0 hr$^{-1}$.

3. A process according to claim 1 wherein the feedstock is depitched tall oil.

4. A process according to claim 1 wherein the tall oil contains about 5–15 wt % unsaponifiables.

5. A process according to claim 3 wherein the tall oil feedstock has a sulphur compound added thereto prior to hydroprocessing, to avoid the loss of sulphided active sites on the catalyst surface and maintain catalyst activity.

6. A process according to claim 1 wherein the feedstock is a blend of said tall oil with a plant or vegetable oil containing at least 20 wt % of unsaturated fatty acids.

7. A process according to claim 6 wherein the plant or vegetable oil is selected from canola oil, sunflower oil, soybean oil, rapeseed oil and palm oil.

8. A process according to claim 1 wherein the feedstock is a blend of said tall oil with an animal fat selected from yellow grease and animal tallow.

9. A process according to claim 6 wherein the tall oil and the plant or vegetable oil are in the ratio of 50–90% tall oil to 50-10% plant or vegetable oil.

10. A process according to claim 8 wherein the tall oil and animal fat are in the ratio of 50–90% tall oil to 50-10% animal fat.

* * * * *